US011801068B2

(12) United States Patent
Ma

(10) Patent No.: US 11,801,068 B2
(45) Date of Patent: Oct. 31, 2023

(54) SHEATHED CUTTING DEVICE

(71) Applicant: William Ma, Zionsville, IN (US)

(72) Inventor: William Ma, Zionsville, IN (US)

(*) Notice: Subject to any disclaimer, the term of this patent is extended or adjusted under 35 U.S.C. 154(b) by 70 days.

(21) Appl. No.: 16/769,485

(22) PCT Filed: Oct. 14, 2019

(86) PCT No.: PCT/US2019/056041
§ 371 (c)(1),
(2) Date: Jun. 3, 2020

(87) PCT Pub. No.: WO2020/263295
PCT Pub. Date: Dec. 30, 2020

(65) Prior Publication Data
US 2021/0401449 A1 Dec. 30, 2021

Related U.S. Application Data

(60) Provisional application No. 62/866,589, filed on Jun. 25, 2019.

(51) Int. Cl.
A61B 17/3211 (2006.01)
A61B 17/00 (2006.01)

(52) U.S. Cl.
CPC . *A61B 17/3211* (2013.01); *A61B 2017/00747* (2013.01); *A61B 2017/00907* (2013.01); *A61B 2017/32113* (2013.01)

(58) Field of Classification Search
CPC ...... A61B 17/3211; A61B 2017/00747; A61B 2017/00907; A61B 2017/32113; A61B 5/150022; A61B 5/15019; A61B 5/150442; A61B 5/150977; A61B 5/15105; A61B 5/15194; A61B 17/205; A61B 17/32053
(Continued)

(56) References Cited

U.S. PATENT DOCUMENTS 3,208,452 A * 9/1965 Stern ............... A61B 10/02
606/183
5,147,303 A 9/1992 Martin
(Continued)

FOREIGN PATENT DOCUMENTS

GB 2 216 805 A 10/1989
KR 1020170114857 A 10/2017

OTHER PUBLICATIONS

International Search Report, International Searching Authority, PCT/US2019/056041, dated Dec. 23, 2019.
(Continued)

*Primary Examiner* — Kathleen S Holwerda
*Assistant Examiner* — Serenity A Miller
(74) *Attorney, Agent, or Firm* — Reichel Stohry Dean LLP; Mark C. Reichel; Natalie J. Dean

(57) ABSTRACT

Sheathed cutting device. An exemplary device for discreetly piercing a skin of a patient can comprise a body having a proximal end and a distal end, a cutting member attached to a plunger, the cutting member and the plunger positioned at least partially within the body, and a biasing member configured to bias the cutting member to an initial position whereby the cutting member is positioned fully within the body, wherein the plunger is slidable into the proximal end of the body, causing the cutting member to extend from the distal end of the body.

19 Claims, 10 Drawing Sheets

(58) Field of Classification Search
USPC .................................... 606/133, 167, 187
See application file for complete search history.

(56) References Cited

U.S. PATENT DOCUMENTS

| | | | |
|---|---|---|---|
| 5,407,436 A | 4/1995 | Toft et al. | |
| 5,916,230 A * | 6/1999 | Brenneman | A61B 5/150412 |
| | | | 606/172 |
| 6,086,545 A * | 7/2000 | Roe | A61B 5/150412 |
| | | | 600/583 |
| 6,299,626 B1 | 10/2001 | Viranyi | |
| 2002/0103499 A1* | 8/2002 | Perez | A61B 5/14514 |
| | | | 606/182 |
| 2002/0188223 A1* | 12/2002 | Perez | A61B 5/14514 |
| | | | 600/573 |
| 2004/0215226 A1* | 10/2004 | Majlessi | A61B 17/00008 |
| | | | 606/190 |
| 2004/0225311 A1 | 11/2004 | Levaughn et al. | |
| 2004/0249405 A1* | 12/2004 | Watanabe | A61B 5/15194 |
| | | | 606/181 |
| 2005/0096586 A1 | 5/2005 | Trautman et al. | |
| 2006/0255215 A1 | 11/2006 | Carnevali | |
| 2007/0083222 A1 | 4/2007 | Schraga | |
| 2010/0185224 A1 | 7/2010 | Wu et al. | |
| 2012/0143086 A1* | 6/2012 | Jacobs | A61B 5/1513 |
| | | | 600/583 |
| 2014/0052165 A1* | 2/2014 | Bilenski | A61B 17/3211 |
| | | | 606/170 |
| 2015/0057604 A1 | 2/2015 | Arami et al. | |
| 2015/0141098 A1 | 5/2015 | Mulder et al. | |
| 2015/0165129 A1 | 6/2015 | Row et al. | |
| 2016/0339223 A1 | 11/2016 | Scherr et al. | |
| 2017/0000952 A1 | 1/2017 | Leary | |
| 2017/0232160 A1 | 8/2017 | Cardwell | |

OTHER PUBLICATIONS

Written Opinion of the International Searching Authority, International Searching Authority, PCT/US2019/056041, dated Dec. 23, 2019.

European Patent Office, Extended European search report and European search opinion, European Application EP19935450.7, dated Jun. 5, 2023.

* cited by examiner

SHEATHED CUTTING DEVICE

PRIORITY & RELATED APPLICATION

The present international patent application is related to, and claims the priority benefit of, U.S. Provisional Patent Application Ser. No. 62/866,589, filed Jun. 25, 2019, the contents of which are incorporated herein directly and by reference in their entirety.

BACKGROUND

Certain skin conditions, such as boils, can be treated by making an incision. While this can be accomplished using a surgical blade, this method of treatment assumes a patient that is at ease with the procedure. Some patients, for example pediatric patients, suffering from said skin conditions are more likely to react negatively to seeing a surgical blade. Reactions may include increased anxiety and fear to the extent that the patient may be uncooperative and attempt to refuse treatment.

Furthermore, and with respect to boils, for example, boils are frequently under pressure such that should the boil be pierced (via an initial incision), pus or other purulent material within the boil could "explode," such as to eject said pus or other purulent material, including infectious organisms, onto the medical personnel using a surgical blade to open the boil. This causes a great risk of pus or other purulent material contacting open orifices of the medical personnel or the patient, such as the eyes, nose, mouth, and/or skin.

Therefore, there is a need for a device that can introduce a precise incision without adding anxiety to the procedure, and that can also protect the user of the device from coming into contact with the pus or other purulent material. Further desired benefits may include the simplification of the procedure while keeping the procedure fast and accurate

BRIEF SUMMARY

The present disclosure includes embodiments of a sheathed cutting device that can prevent patients from observing the incision procedure. Additionally, the device is able to introduce quick and accurate incisions without introducing anxiety or fear.

In an exemplary embodiment of a device for a sheathed cutting device of the present disclosure, the device comprises a body having a proximal and distal end, a cutting member attached to a plunger, both housed at least partially within the body; a biasing member configured to bias the cutting member to an initial position wherein the cutting member is fully within the body; and wherein the plunger is slidable into the proximal end of the body and the cutting member is extendable from the distal end of the body.

In another embodiment, the biasing member is disposed around the plunger. In a further embodiment, the biasing member is connected to the plunger at a first end and to the body at a second end. In another embodiment, the biasing member is disposed within the body. In another embodiment, the biasing member is disposed external to the body.

In another embodiment, the cutting member is a blade or a plurality of needles

In another embodiment, the device further comprises a depth adjustment member.

In another embodiment, a device for discreetly piercing a skin of a patient, the device comprises a body having a proximal and distal end, a cutting member attached to a plunger, both housed at least partially within the body; a biasing member configured to bias the cutting member to an initial position wherein the cutting member is fully within the body; a cup portion on the distal end of the body; and wherein the plunger is slidable into the proximal end of the body and the cutting member is extendable from the distal end of the body.

In another embodiment, the cup portion is flared. In another embodiment, the cup portion is at least partially opaque.

The present disclosure includes disclosure of a device for discreetly piercing a skin of a patient, the device comprising a body having a proximal end and a distal end, a cutting member attached to a plunger, the cutting member and the plunger positioned at least partially within the body, and a biasing member configured to bias the cutting member to an initial position whereby the cutting member is positioned fully within the body, wherein the plunger is slidable into the proximal end of the body, causing the cutting member to extend from the distal end of the body.

In at least one embodiment, the biasing member is disposed around the plunger. In at least one embodiment, the biasing member is connected to the plunger at a first location and is connected to the body at a second location. In at least one embodiment, the biasing member is disposed within the body. In at least one embodiment, the biasing member is disposed external to the body. In at least one embodiment, the cutting member is a blade. In at least one embodiment, the cutting member is a plurality of needles. In at least one embodiment, the device further comprises a depth adjustment member coupled to the device, the depth adjustment configured to adjust a distance the cutting member can extend from the body.

In at least one embodiment, the device further comprises a cup portion coupled to or formed as part of the body, the cup portion extending from the body outward and toward the distal end of the body. In at least one embodiment, the cup portion has a circumferential distal portion. In at least one embodiment, the cup portion is opaque. In at least one embodiment, the cup portion has a transparent portion and a non-transparent portion. In at least one embodiment, the cup portion is opaque or translucent, and wherein the cup portion defines a window therein. In at least one embodiment, the body further comprises a grip. In at least one embodiment, the grip extends outward from the body. In at least one embodiment, the grip is defined as an indentation within the body.

In at least one embodiment, the device is configured so that when in use, and when the plunger is depressed and the distal end of the body contacts a patient's skin, the cutting member can pierce the patient's skin. In at least one embodiment, the device is configured so that when in use, and when the plunger is depressed and the distal end of the body contacts a patient's skin, the cutting member can pierce a boil or other skin condition of the patient's skin. In at least one embodiment, the device is configured so that when in use, and when the plunger is depressed and when the cup portion contacts a patient's skin, the cutting member can pierce the patient's skin. In at least one embodiment, the device is configured so that when in use, and when the plunger is depressed and when the cup portion contacts a patient's skin, the cutting member can pierce a boil or other skin condition of the patient's skin.

In at least one embodiment, the device is configured so that any pus or other material erupting from the boil or other skin condition is contained within the cup portion until the device no longer contacts the patient's skin.

The present disclosure includes disclosure of a device for discreetly piercing a skin of a patient, the device comprising a body having a proximal end and a distal end, a cutting member attached to a plunger, the cutting member and the plunger positioned at least partially within the body, a biasing member configured to bias the cutting member to an initial position whereby the cutting member is positioned fully within the body, a depth adjustment member coupled to the device, the depth adjustment configured to adjust a distance the cutting member can extend from the body, and a cup portion coupled to or formed as part of the body, the cup portion extending from the body outward and toward the distal end of the body, wherein the plunger is slidable into the proximal end of the body, causing the cutting member to extend from the distal end of the body. In at least one embodiment, the body further comprises a grip. In at least one embodiment, the grip extends outward from the body. In at least one embodiment, the grip is defined as an indentation within the body.

The present disclosure includes disclosure of a device for discreetly piercing a skin of a patient, the device comprising a body having a proximal end and a distal end, a cutting member attached to a plunger, the cutting member and the plunger positioned at least partially within the body, a biasing member configured to bias the cutting member to an initial position whereby the cutting member is positioned fully within the body, and a cup portion coupled to or formed as part of the body, the cup portion extending from the body outward and toward the distal end of the body, wherein the plunger is slidable into the proximal end of the body, causing the cutting member to extend from the distal end of the body, and wherein the body further comprises a grip.

In at least one embodiment, the device further comprises a draft adjustment member coupled to the device, the depth adjustment configured to adjust a distance the cutting member can extend from the body.

The present disclosure includes disclosure of a piercing method, the method comprising the step of positioning a device of the present disclosure relative to a patient's skin so that the distal end of the body contacts a patient's skin, and depressing the plunger to cause the cutting member to pierce the patient's skin.

The present disclosure includes disclosure of a piercing method, the method comprising the step of positioning a device of the present disclosure relative to a patient's skin so that the distal end of the body contacts a patient's skin, and depressing the plunger to cause the cutting member to pierce a boil or other skin condition of the patient's skin.

The present disclosure includes disclosure of a method, comprising the steps of positioning a portion of a device relative to a patient's skin, the device comprising a body having a proximal end and a distal end, a cutting member attached to a plunger, the cutting member and the plunger positioned at least partially within the body, and a biasing member configured to bias the cutting member to an initial position whereby the cutting member is positioned fully within the body, and depressing the plunger to cause the cutting member to extend from the distal end of the body so to pierce the patient's skin or a boil or other skin condition of the patient's skin.

In at least one embodiment, the device further comprises a cup portion coupled to or formed as part of the body, the cup portion extending from the body outward and toward the distal end of the body, and wherein the positioning step comprises the step of positioning the cup portion onto the patient's skin.

In at least one embodiment, the step of depressing the plunger is performed to case the cutting member to pierce the patient's skin, causing blood to erupt from the patient's skin, whereby the blood is contained within the cup portion.

In at least one embodiment, the step of depressing the plunger is performed to case the cutting member to pierce the boil or other skin condition of the patient's skin, causing pus or other purulent material or to erupt from the boil or other skin condition of the patient's skin, whereby the pus or other purulent material is contained within the cup portion.

In at least one embodiment, the cup portion has a window defined therein, and wherein the positioning step is performed to position the cup portion so that the cup portion faces a user of the device.

In at least one embodiment, the cup portion has a transparent portion and a non-transparent portion, and wherein the positioning step is performed to position the cup portion so that the transparent portion of the cup portion faces a user of the device.

In at least one embodiment, the device further comprises a depth adjustment member coupled to the device, the depth adjustment configured to adjust a distance the cutting member can extend from the body, and wherein the method further comprises the step of adjusting the depth adjustment member to a desired depth prior to the step of depressing the plunger.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
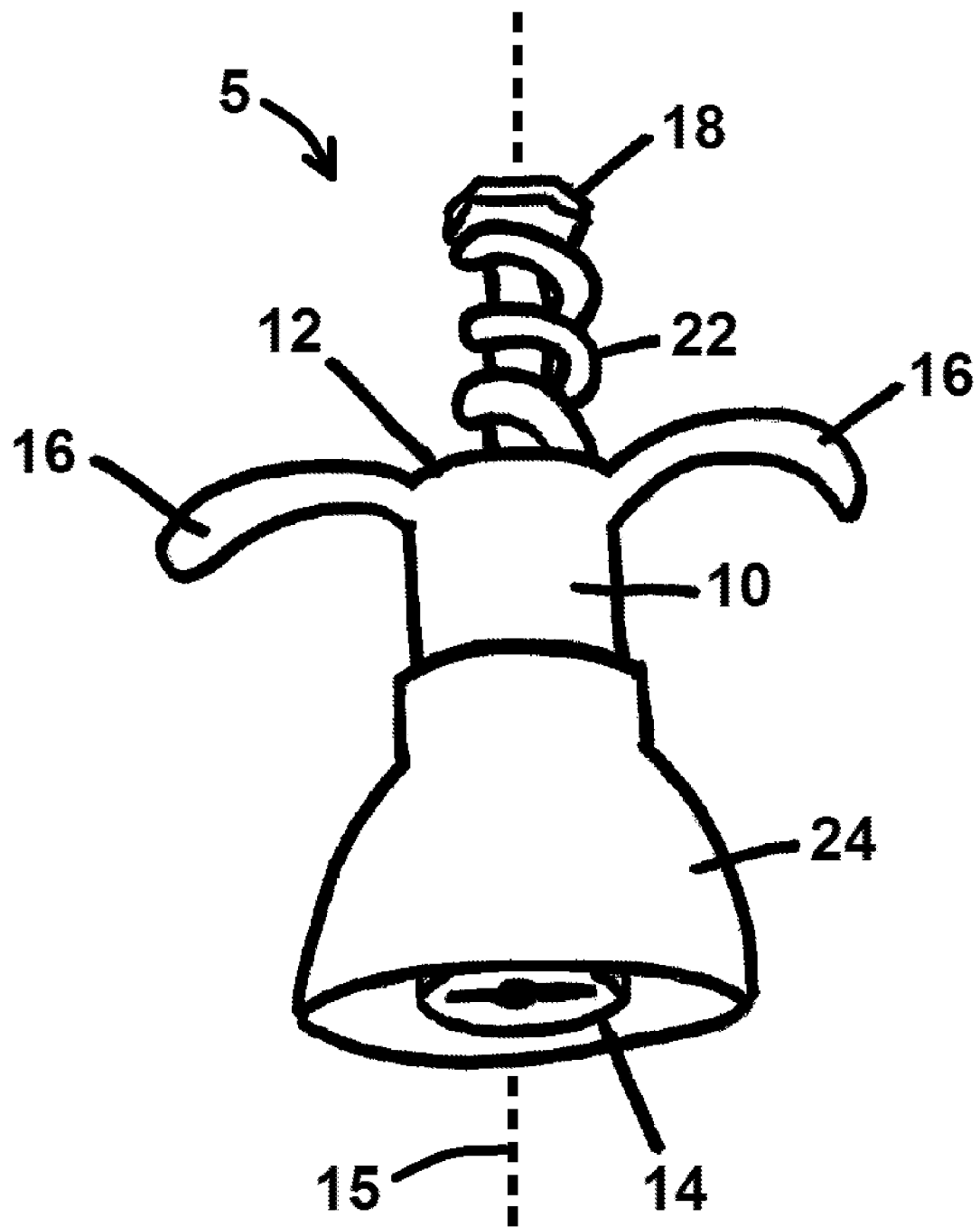
FIG. 1 shows a side view of a device, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 4:
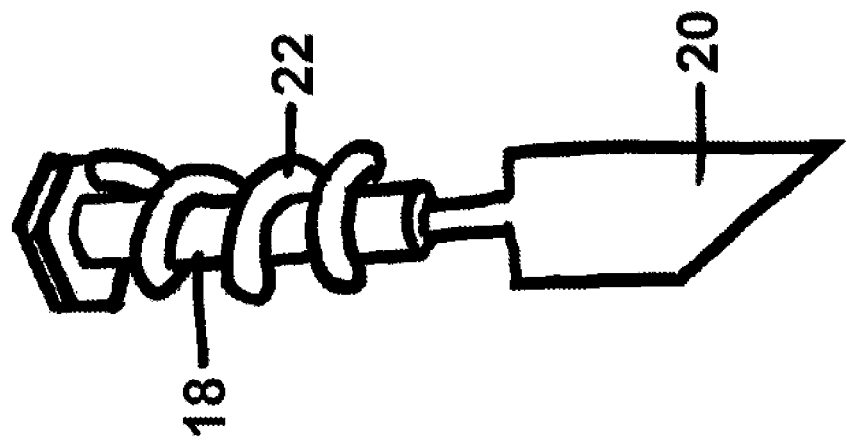
FIG. 4 shows a component view of portions of a plunger, cutting member, and biasing member, according to an exemplary embodiment of the present disclosure.
Figure 3:
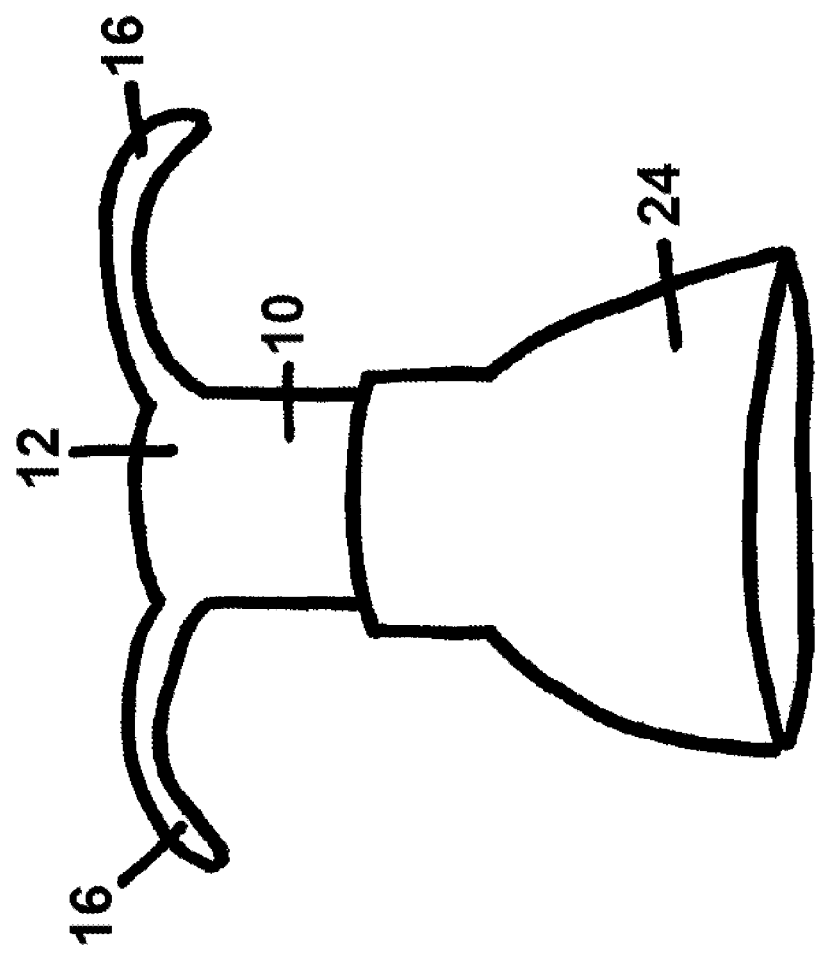
FIG. 3 shows a component view of portions of a device, according to an exemplary embodiment of the present disclosure.
Figure 5:
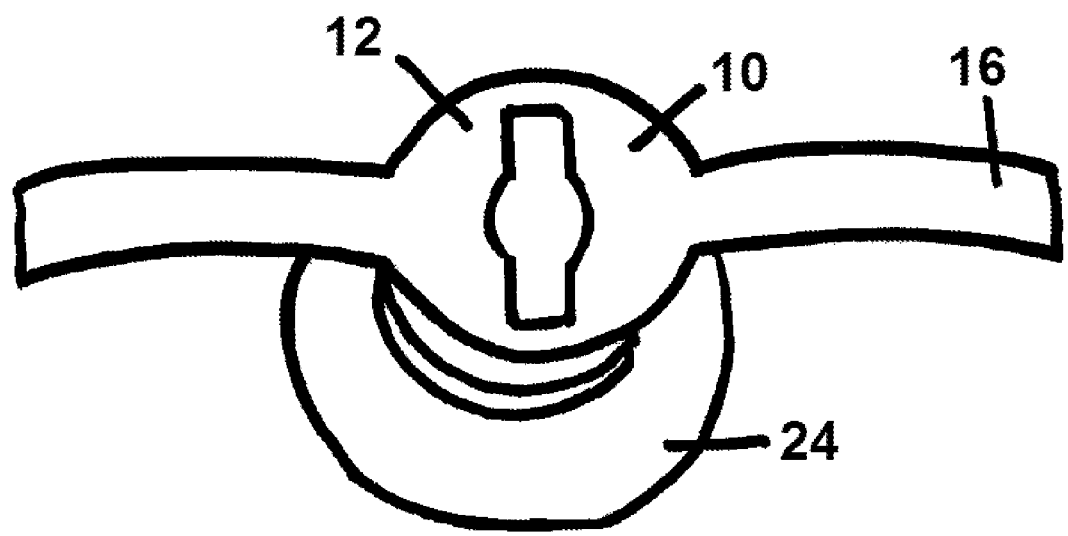
FIG. 5 shows a top perspective view of a body component of a device, according to an exemplary embodiment of the present disclosure.

In an exemplary embodiment, an exemplary sheathed cutting device 5 for treating boils and other skin conditions of the present disclosure is shown in FIGS. 1-5. As shown in FIGS. 1-5, the device 5 comprises a body 10, and a cutting member 20 attached to plunger 18, wherein the cutting member 20 and plunger 18 are positioned at least partially inside the body 10. In a preferred embodiment the body 10 is generally cylindrical or barrel shaped and the cutting member 20 and plunger 18 (collectively referred to as parts of a cutting assembly 23 as shown in FIG. 4) extend along a longitudinal axis 15 of the body 10. The body 10 may also comprise two grips 16 disposed circumferentially on the body 10 or otherwise extending or protruding from body 10 to aid in manipulating the device 5 and plunger 18.

Preferably, the cutting member 20 is a blade, such as a surgical blade as in the embodiment shown in FIG. 1. Cutting member 20 may be other types of member(s) or object(s) capable of piercing or otherwise penetrating the skin, such as a plurality of needles.

The plunger 18 is located at or near the proximal end 12 of the body 10 and slidable further into the body 10. As the cutting member 20 is attached to the plunger 18, the movement of the plunger 18 causes corresponding movement of the cutting member 20. That is, the clinician or other medical personnel can extend at least part of the cutting member 20 from the distal end 14 of the body 10, through distal opening 19, by pressing the plunger 18 into the body 10 from the proximal end 12 of the body 10, such as in the direction indicated by arrow A in FIG. 2.

Devices 5 of the present disclosure can further comprise a biasing member 22. The biasing member 22 biases the plunger 18, and the corresponding cutting member 20, to a position where the cutting member 20 is wholly within the body 10, and thus hidden inside as shown in FIG. 1. The biasing member 22 is preferably a spring element (a spring), or it can be another element, such as a flexible plastic element or a flexible metal element.

In the embodiment of FIGS. 1-5, the biasing member 22 is a spring is disposed external to the body 10 and surrounding the plunger 18. A first end of the spring is adjacent and/or coupled to a portion of the plunger 18, and a second end of the spring is adjacent and/or coupled to the body, such as at the proximal end 12 of the body 10. This positioning causes the biasing member to push (exert a force) the plunger 18 and body 10 away from each other, retracting the cutting member 20 into the body 10, such as shown in FIG. 1.

Figure 2:
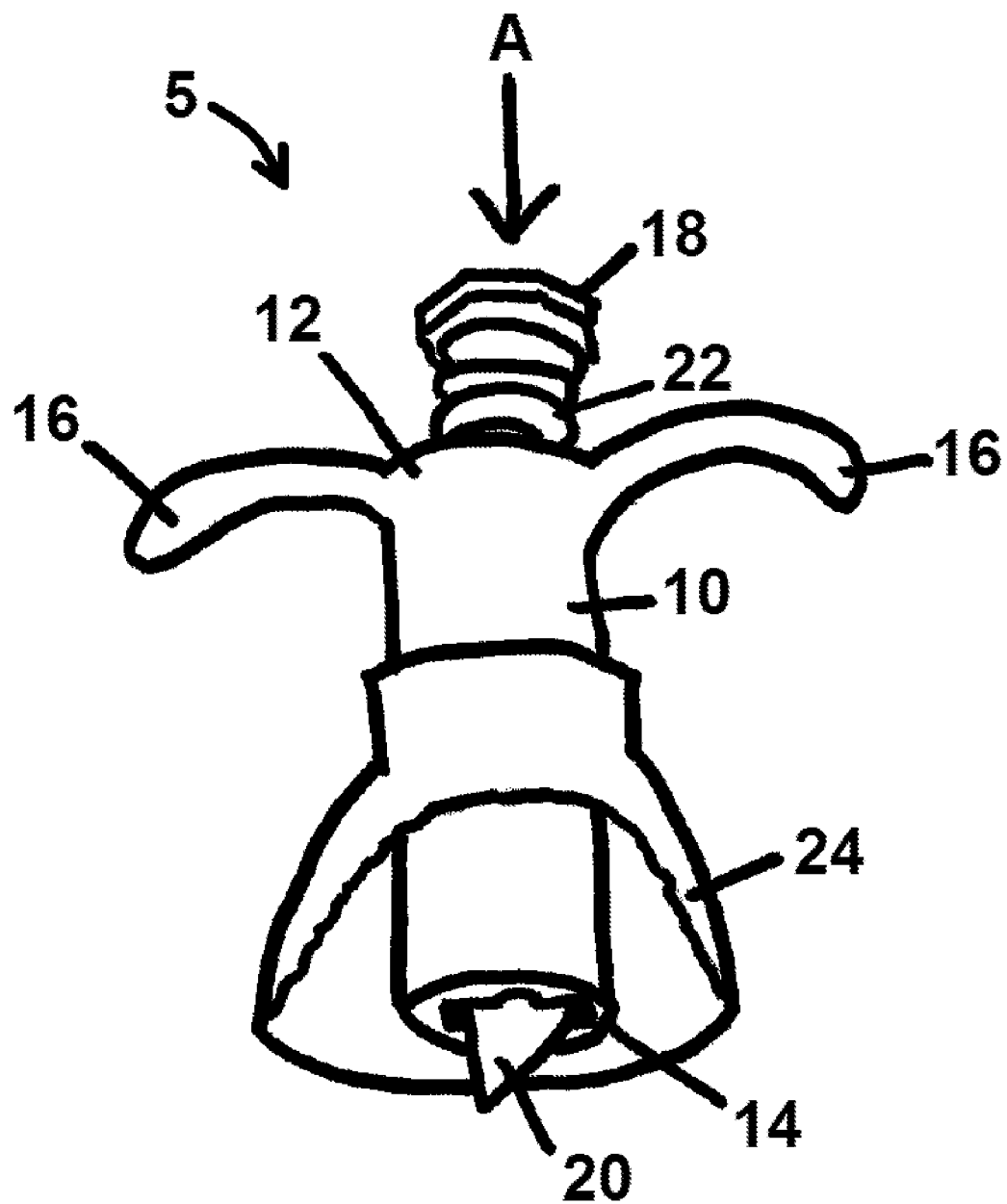
FIG. 2 shows a partial cutaway of a side view of a device having a cutting member extended, according to an exemplary embodiment of the present disclosure.

Pressing the plunger 18 into the body 10 in the direction indicated by arrow A in FIG. 2 will extend the cutting member 20 from the distal end 14 of the body 10 and compress the spring. Upon release of the plunger 18, the compressed spring will force the plunger 18 end and device 5 body 10 apart thereby retracting the cutting member 20 into the body 10 as shown in FIG. 1.

The exemplary embodiment pictured in FIGS. 1-5 also comprises an optional cup 24 portion. The cup portion 24 may be formed separately, as shown in FIGS. 1-5, or may be integral with the body 10. During use, the cup portion 24 is placed over the treatment area (a location on the skin of a patient) such that the treatment area is shrouded, shielded, or otherwise hidden from view, at least partially, by the cup portion 24. The cup portion 24 is preferably flared, namely extending relatively outward and down from a relative center of the body 10. Cup portion 24 can be rigid or formed of a soft material, such as a pliable or flexible plastic or other polymer-based material, so that it may be placed comfortably against a patient's body. Cup portion 24 may vary in shape or composition as necessary for the procedure.

The cup portion 24 may comprise or have varying levels of opacity, ranging anywhere between or from fully opaque, translucent, or fully transparent. An opaque cup portion 24 prevents the patient from seeing the procedure from being performed, namely the piercing of the skin by cutting member 20, thereby reducing patient anxiety. Similarly, a translucent cup portion 24 can partially obscure the procedure, but also has the advantage of allowing some observation of the procedure. This can be useful if the clinician desires to confirm the alignment of the device 5 and treatment site, or to observe for the presence of blood, which indicates the patient's skin has been penetrated. The cup portion 24 could also comprise a portion comprising a first level of opacity and a second portion comprising a second level of opacity, such as where half (or a portion) of the cup portion 24 is opaque and half (or portion) is transparent. Other cup portion 24 embodiments could have a translucent portion and a transparent portion, or an opaque portion and a translucent portion. The opaque section (or translucent portion) of the cup portion 24 can be oriented to face the patient, and the transparent portion (or the translucent portion) of the cup portion 24 can be oriented toward the clinician. The cup portion 24 could also be rotatable around the body 10 to orient the various portions of the cup portion 24 appropriately.

Figure 6:
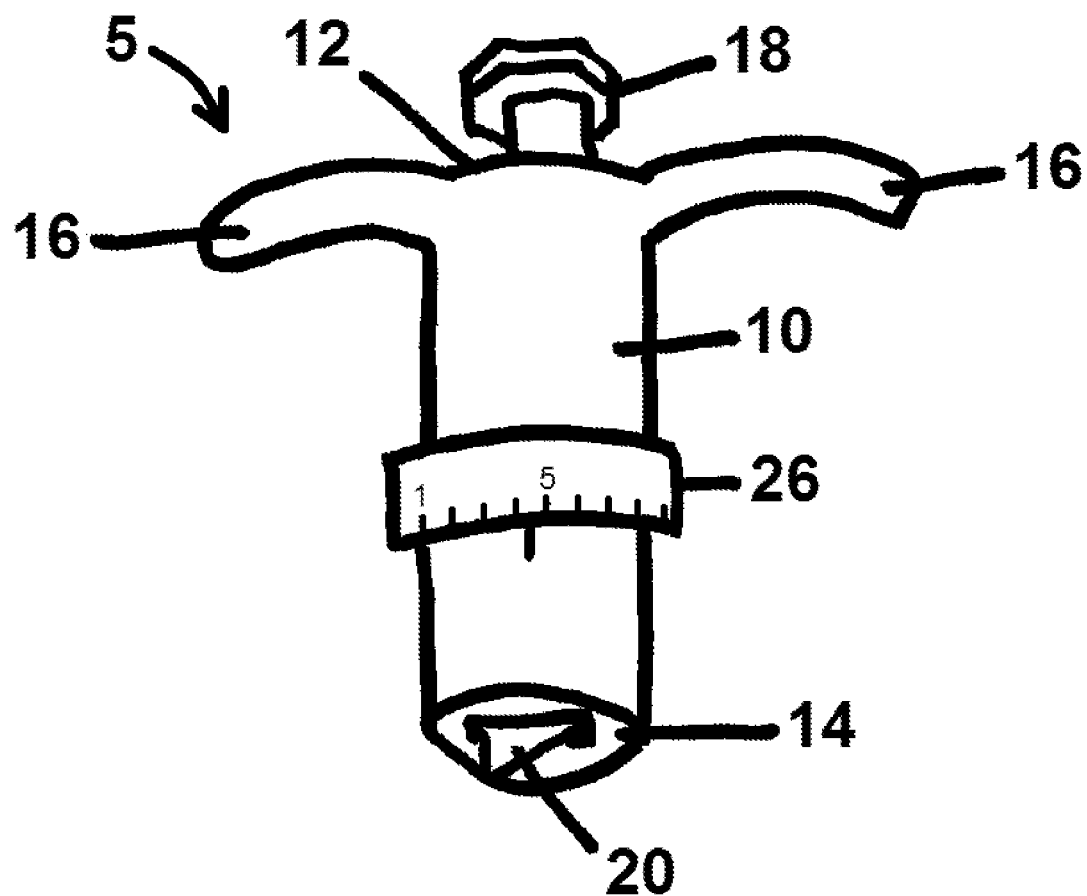
FIG. 6 shows a side view of a device, according to an exemplary embodiment of the present disclosure.

The device 5 may also include a depth adjustment member 26 as shown in FIG. 6. For example, the device 5 may comprise a depth adjustable member 26, such as one configured as a rotatable ring, disposed on the body 10, wherein rotation of the ring adjusts the degree/extent of movement the plunger 18 is capable of and therefore the depth the cutting member 20 will penetrate into the treatment area when the plunger 18 is depressed.

Figure 7:
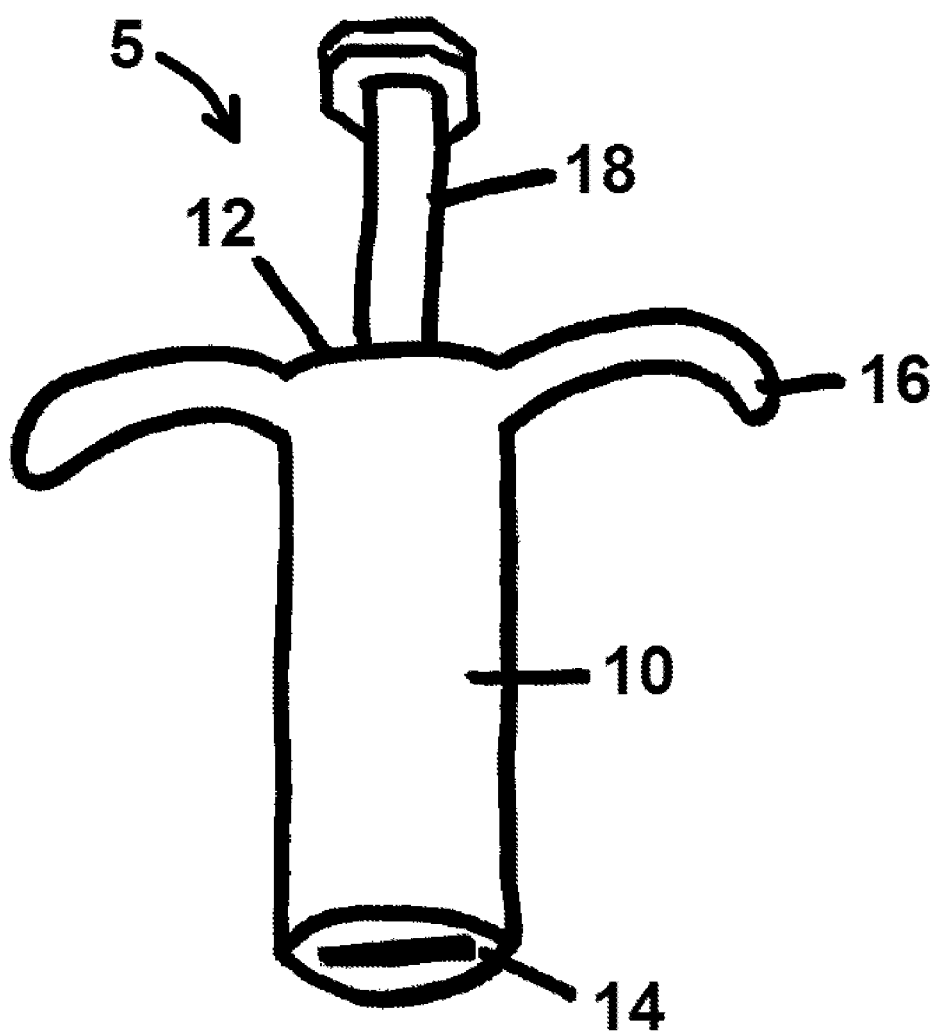
FIG. 7 shows a side view of a device, according to an exemplary embodiment of the present disclosure.
Figure 8:
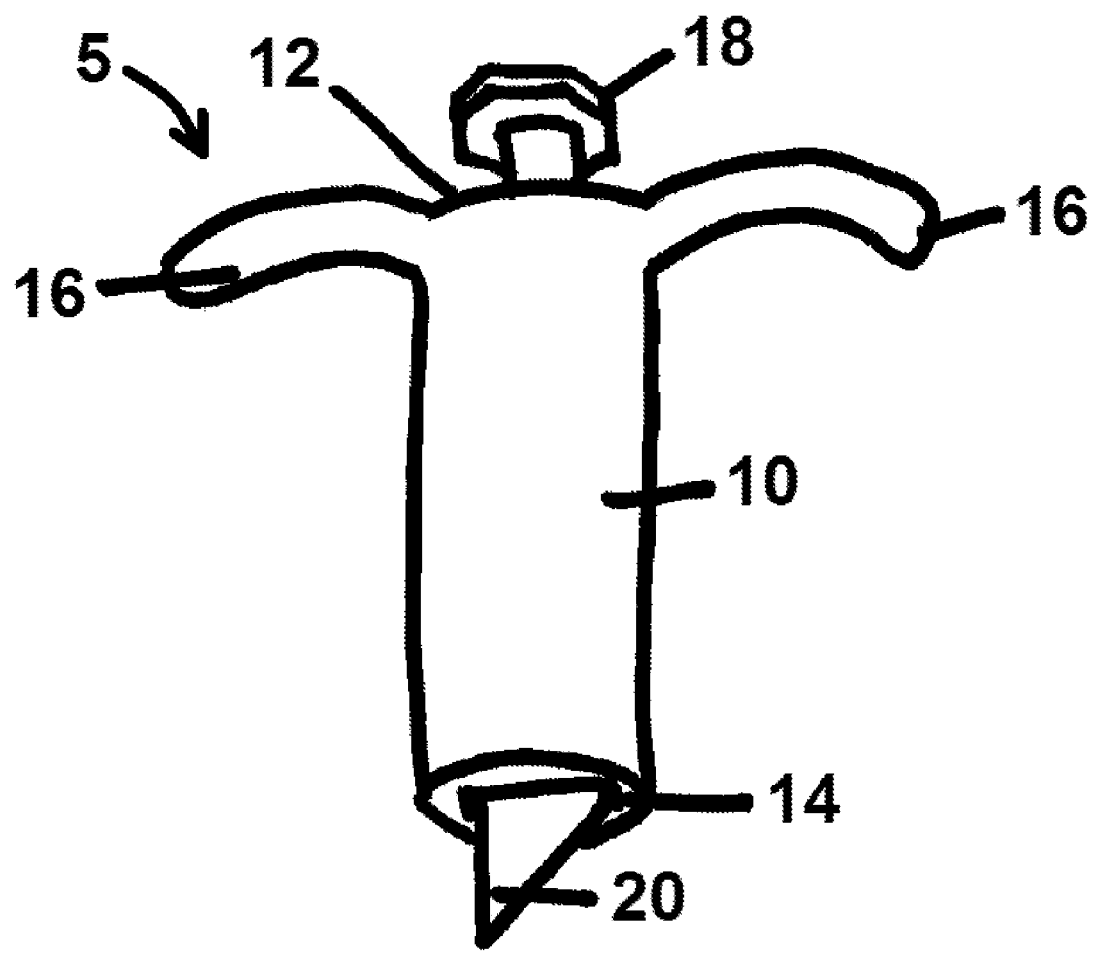
FIG. 8 shows a side view of a device having a cutting member comprising a blade extended therefrom, according to an exemplary embodiment of the present disclosure.

In an additional embodiment, as shown in FIGS. 7 and 8, the device 5 comprises a plunger 18, a cutting member 20, and a body 10 as described in the embodiment of FIGS. 1-5. Similar to the embodiment of FIGS. 1-5, the plunger 18 and cutting member 20 of the embodiment of FIGS. 7 and 8 are attached and located at least partially within the body 10. The plunger 18 may be pressed into the body 10, which then extends the cutting member 20 out of the body 10. As shown in FIGS. 7 and 8, the body 10 may also comprise two grips 16 to aid in manipulating the device 5.

The second embodiment of FIGS. 7 and 8 further comprises a biasing member 22, such as a spring. The biasing member 22 of the embodiment of FIGS. 7 and 8 is disposed around the plunger 18 and within the body 10. In this embodiment, the spring is hidden from view. The spring is configured to bias the plunger 18 out of the proximal end 12 of the body 10 which biases the cutting member 20 into the body 10 so that the cutting member 20 is withdrawn into the body 10.

Figure 9:
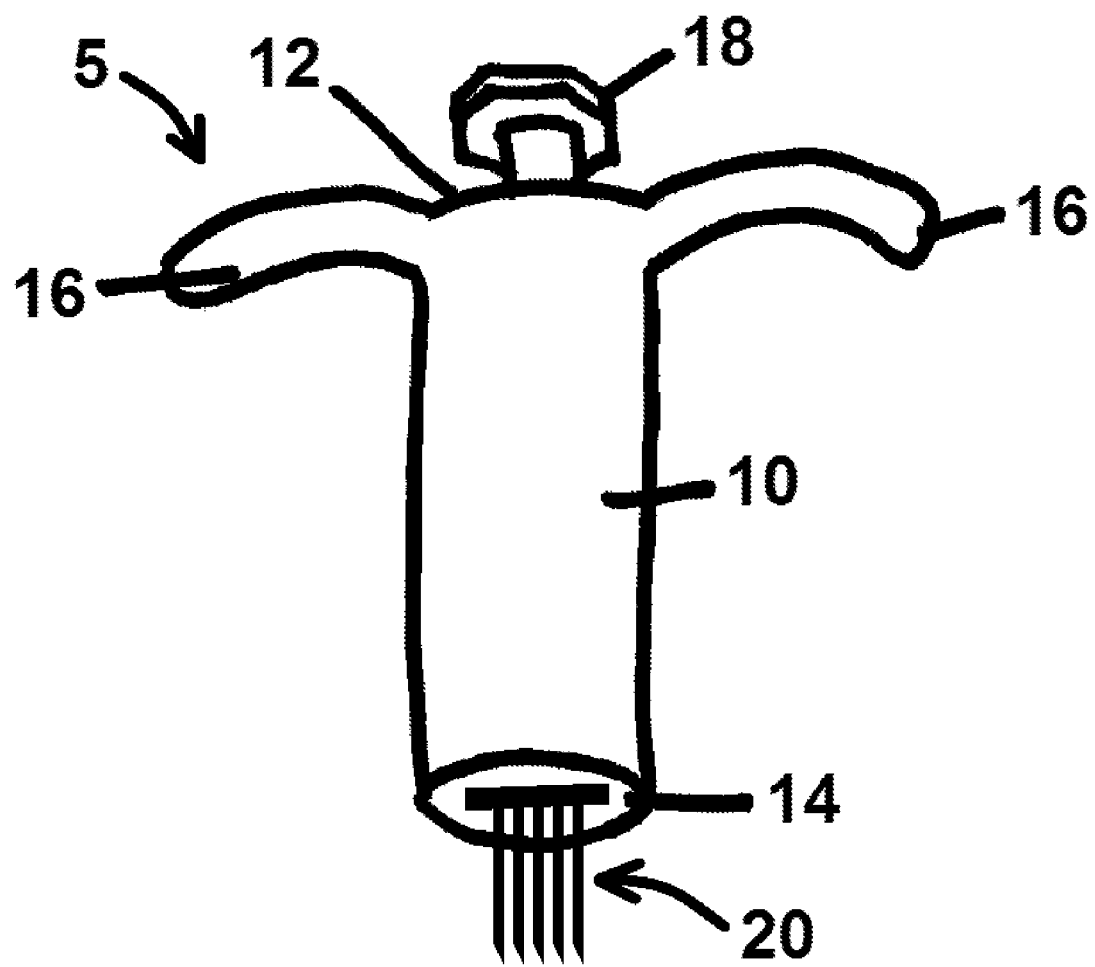
FIG. 9 shows a side view of a device having a cutting member comprising needles extended therefrom, according to an exemplary embodiment of the present disclosure.

FIG. 9 shows an exemplary embodiment of a device 5 of the present disclosure, whereby the cutting member 20 comprises a plurality of needles, as referenced herein.

Devices 5, as shown in FIGS. 6-9, can also comprise a cup portion 24 as referenced herein.

The embodiments of the present disclosure may be used to treat boils, pimples, and other conditions that cannot be properly addressed using a needle. Since a blade is used, an incision is formed rather than just a small opening, by way of cutting member 20. Where the cutting member 20 comprises a plurality of needles, a large number of openings are formed, creating a similar effect to using a blade.

With respect to boils, for example, boils are frequently under pressure such that should the boil be pierced (via an initial incision), pus or other purulent material within the boil could "explode," such as to eject said pus or other purulent material, including infectious organisms, onto the user of the device 5, and in particular into open orifices such as the eyes, nose, mouth, and/or skin. The inclusion of a cup portion 24 therefore operates to prevent splatter of said pus or other purulent material, which can lessen anxiety of the medical personnel using said device 5.

A method of use of the present disclosure involves placing the distal end 14 of the body 10 or the cup portion 24 against the treatment area. The cutting member 20 is initially in a withdrawn position due to the actions of the biasing member 22. The device 5 is aligned with the treatment site, so that upon depressing the plunger 18, the cutting member 20 will contact the treatment site and break/pierce the skin of the patient. Where the embodiment being used comprises a cup portion 24, a translucent or transparent cup portion 24 will allow the clinician to ascertain the alignment of the device 5 and the treatment site. If the embodiment being used includes a depth adjustment member 26, the desired depth should be set before extending the cutting member 20. Upon confirming correct alignment, the clinician can depress the plunger 18 into the body 10 which extends the cutting member 20 into the patient's skin. A transparent or translucent cup portion 24 allows the clinician to observe the cutting member 20, and also observe for the presence of blood, confirming successful treatment. An opaque cup portion 24 will prevent the patient from observing the action of the cutting member 20, thereby reducing anxiety.

Figure 10:
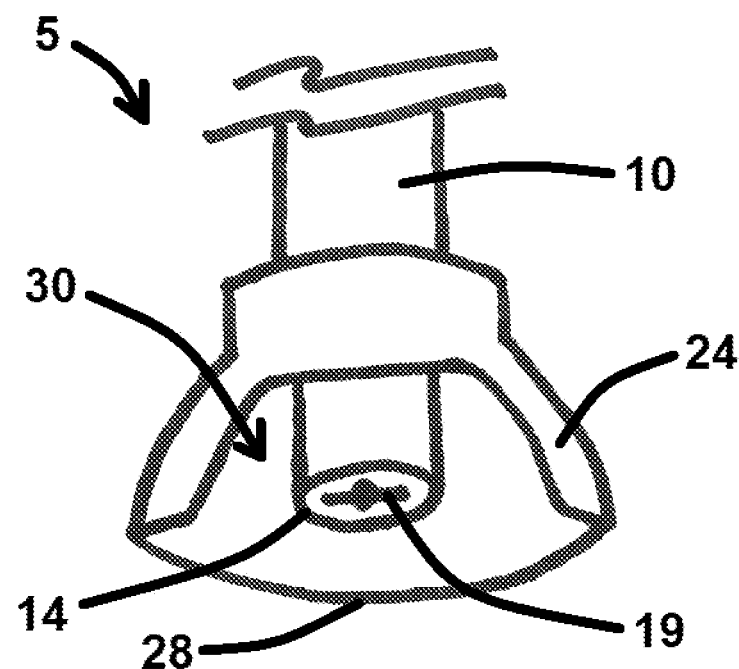
FIG. 10 shows a distal portion of a device having a cup portion with a window defined therein, according to an exemplary embodiment of the present disclosure.
Figure 11:
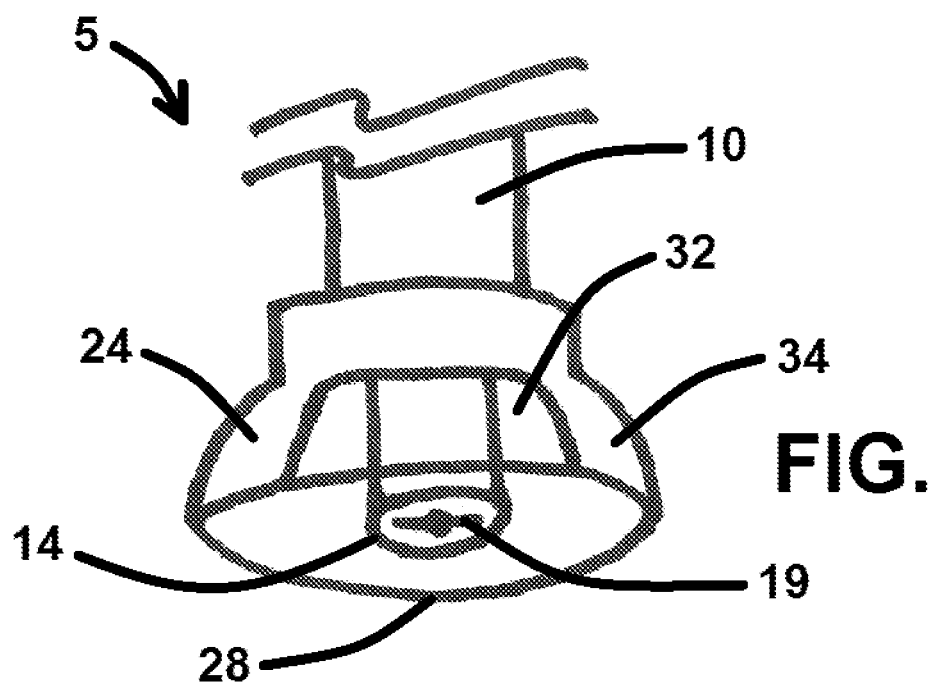
FIG. 11 shows a distal portion of a device having a cup portion with a transparent portion and a non-transparent portion, according to an exemplary embodiment of the present disclosure.

FIGS. 10 and 11 show additional embodiments of distal portions of devices 5 of the present disclosure. As shown in FIG. 10, a cup portion 24 of an exemplary device 5 of the present disclosure can have a distal portion 28 that is not fully circumferential, whereby cup portion 24 defines a window therein whereby medical personnel using said device 5 can see the patient's skin underneath cup portion 24 during a lancing procedure. Window 30 can be defined within any portion of cup portion 24, such as on a relative side of cup portion at or away from distal portion 28.

The embodiment shown in FIG. 11, a cup portion 24 of an exemplary device 5 of the present disclosure can have a distal portion 28 that is fully circumferential, whereby cup portion 24 has a transparent or relatively transparent (from transparent to translucent, including translucent) portion, referenced herein as transparent portion 32, and further has a translucent to opaque, including opaque) portion, referenced herein as non-transparent portion 34. In such an embodiment, medical personnel using said device 5 can see the patient's skin underneath cup portion 24 through transparent portion 32 positioned in view of the medical personnel, while the patient would not see transparent portion 32, and would instead see non-transparent portion 34, which shields the lancing procedure from the patient's view. The present disclosure includes disclosure of cup portions 24 that can be partially or fully transparent, partially or fully translucent, and/or partially or fully opaque.

Figure 12:
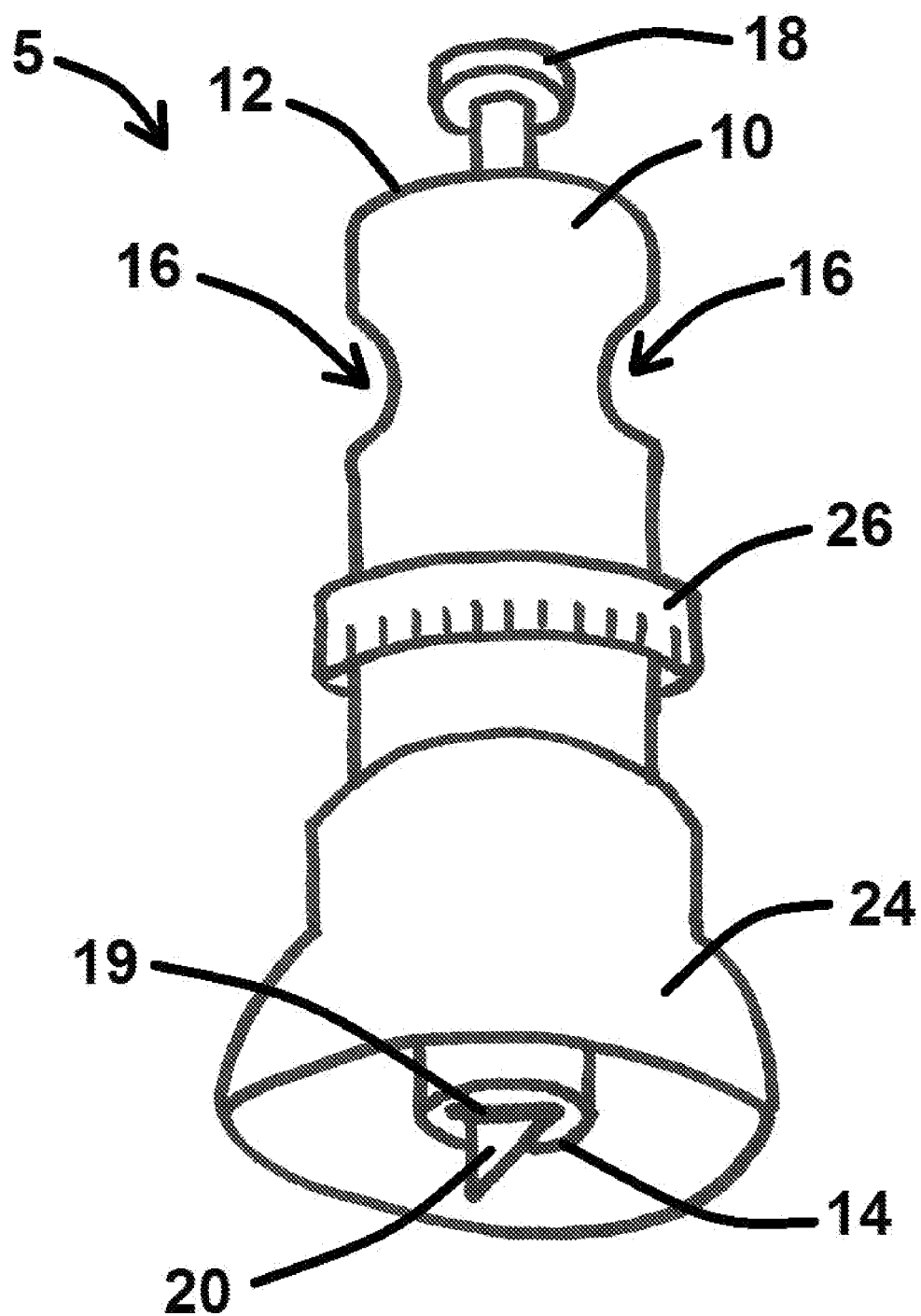
FIG. 12 shows a device having a grip formed as indentions in the body, according to an exemplary embodiment of the present disclosure.

FIG. 12 shows an exemplary embodiment of a device 5 of the present disclosure, whereby said device 5 has one or more grips 16 defined therein, forming effective indentations within body 10 of device 5. As shown in FIGS. 1, 2, and 4-9, grip(s) 16 can extend from body 10 in various embodiments, and the present disclosure is not limited to only one type of grip 16 used with a particular device 5. For example, an exemplary device 5 could have two or more grips 16, with one or more grips 16 extending outward from body 10, and with one or more grips 10 forming indentation(s) within body 10.

While various embodiments of sheathed cutting devices and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

It is within the scope of this disclosure that the various features from the embodiments described above may be combined or removed or otherwise interchangeable. For example, another exemplary embodiment of a device 5 may comprise a cup portion 24 and a biasing member 22 disposed within the body 10 of the device. Another exemplary embodiment may comprise a rotatable depth adjustment ring 26 and a biasing member 22 disposed inside the body 10.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device for discreetly piercing a skin of a patient, the device comprising:
   a body having a proximal end and a distal end;
   a cutting member attached to a plunger, the cutting member and the plunger positioned at least partially within the body;
   a biasing member configured to bias the cutting member to an initial position whereby the cutting member is positioned fully within the body; and
   a cup portion attached to the body at a proximal end of the cup portion and a distal end of the cup portion extending from the body radially outward and toward the distal end of the body such that any portion of the cup portion not attached to the body has a greater diameter than the body, the cup portion further comprising an opening defined in the distal end of the cup portion, wherein the opening is larger than the body, and the body extends into the distal end of the cup portion;

wherein the cup portion has a transparent portion on one relative side of the cup portion that extends to the distal edge of the cup portion for allowing a user of the device to see a piercing procedure, and a non-transparent portion on the other relative side of the cup portion for shielding the patient from seeing the piercing procedure;

wherein the plunger is slidable into the proximal end of the body, causing the cutting member to extend from the distal end of the body.

2. The device of claim 1, wherein the biasing member is connected to the plunger at a first location and is connected to the body at a second location.

3. The device of claim 1, wherein the biasing member is disposed external to the body and visually exposed to a user of the device.

4. The device of claim 1, wherein the cutting member is a blade.

5. The device of claim 1, wherein the cutting member is a plurality of needles.

6. The device of claim 1, further comprising a depth adjustment member coupled to the device, the depth adjustment member configured to adjust a distance the cutting member can extend from the body.

7. The device of claim 1, wherein the cup portion is coupled to or formed as part of the body, the cup portion having a circumferential distal portion.

8. The device of claim 7, wherein the cup portion is opaque or translucent, and wherein the cup portion defines a window therein.

9. The device of claim 7, configured so that when in use, and when the plunger is depressed and when the cup portion contacts a patient's skin, the cutting member can pierce a boil or other skin condition of the patient's skin.

10. The device of claim 9, configured so that any pus or other material erupting from the boil or other skin condition is contained within the cup portion until the device no longer contacts the patient's skin.

11. A piercing method, the method comprising the step of:
positioning the device of claim 9 relative to a patient's skin so that the cup portion contacts a patient's skin; and
depressing the plunger to cause the cutting member to pierce the patient's skin or a boil or other skin condition of the patient's skin.

12. The device of claim 1, wherein the body further comprises a grip, and wherein the grip comprises two diametrically opposed arc shaped extensions extending laterally outward from the body.

13. The device of claim 1, configured so that when in use, and when the plunger is depressed, the cutting member can pierce a boil or other skin condition of the patient's skin.

14. A piercing method, the method comprising the step of:
positioning the device of claim 1 relative to a patient's skin and depressing the plunger to cause the cutting member to pierce the patient's skin or a boil or other skin condition of the patient's skin.

15. A device for discreetly piercing a skin of a patient, the device comprising:
a body having a proximal end and a distal end and further comprising a grip;
a cutting member attached to a plunger, the cutting member and the plunger positioned at least partially within the body;

a biasing member configured to bias the cutting member to an initial position whereby the cutting member is positioned fully within the body;
a depth adjustment member coupled to the device, the depth adjustment member configured to adjust a distance the cutting member can extend from the body; and
a cup portion coupled to or formed as part of the body and attached to the body at a proximal end of the cup portion, a distal end of the cup portion extending from the body radially outward and toward the distal end of the body such that any section of the cup portion not attached to the body has a greater diameter than the body, and the cup portion further comprising an opening defined in the distal end of the cup portion, wherein the opening is larger than the body, and the body extends into the distal end of the cup portion;
wherein the cup portion has a transparent portion on one relative side of the cup portion that extends to the distal edge of the cup portion for allowing a user of the device to see a piercing procedure, and a non-transparent portion on the other relative side of the cup portion for shielding the patient from seeing the piercing procedure;
wherein the cup portion is made entirely of a soft pliable or flexible material;
wherein the plunger is slidable into the proximal end of the body, causing the cutting member to extend from the distal end of the body.

16. A method, comprising the steps of:
positioning a portion of a device relative to a patient's skin, the device comprising:
a body having a proximal end and a distal end,
a cutting member attached to a plunger, the cutting member and the plunger positioned at least partially within the body,
a biasing member configured to bias the cutting member to an initial position whereby the cutting member is positioned fully within the body, and
a cup portion attached to the body at a proximal end of the cup portion and a distal end of the cup portion extending from the body radially outward and toward the distal end of the body such that any section of the cup portion not attached to the body has a greater diameter than the body, and the cup portion further comprising an opening defined in the distal end of the cup portion, wherein the opening is larger than the body, and the body extends into the distal end of the cup portion, wherein the cup portion has a transparent portion on one relative side of the cup portion that extends to the distal edge of the cup portion for allowing a user of the device to see a piercing procedure, and a non-transparent portion on the other relative side of the cup portion for shielding the patient from seeing the piercing procedure; and
depressing the plunger to cause the cutting member to extend from the distal end of the body to pierce the patient's skin or a boil or other skin condition of the patient's skin.

17. The method of claim 16:
wherein the cup portion is coupled to or formed as part of the body, the cup portion extending from the body outward and toward the distal end of the body, and wherein the positioning step comprises the step of positioning the cup portion onto the patient's skin; and
wherein the device further comprises a depth adjustment member coupled to the device, the depth adjustment member configured to adjust a distance the cutting member can extend from the body, and wherein the method further comprises the step of adjusting the depth adjustment member to a desired depth prior to the step of depressing the plunger.

18. The method of claim 17, wherein the step of depressing the plunger is performed to cause the cutting member to pierce the patient's skin, causing blood to erupt from the patient's skin, whereby the blood is contained within the cup portion.

19. The method of claim 17, wherein the step of depressing the plunger is performed to cause the cutting member to pierce the boil or other skin condition of the patient's skin, causing pus or other purulent material to erupt from the boil or other skin condition of the patient's skin, whereby the pus or other purulent material is contained within the cup portion.

* * * * *